(12) United States Patent
Ishikawa (10) Patent No.: US 11,525,665 B2
(45) Date of Patent: Dec. 13, 2022

(54) OPTICAL COHERENCE TOMOGRAPHIC APPARATUS AND OPTICAL COHERENCE TOMOGRAPHIC METHOD PERFORMING SPECTRUM CONVERSION BASED ON SINGLE GAUSSIAN DISTRIBUTION CURVE

(71) Applicant: SCREEN HOLDINGS CO., LTD., Kyoto (JP)

(72) Inventor: Naoki Ishikawa, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 16/980,716

(22) PCT Filed: Nov. 29, 2018

(86) PCT No.: PCT/JP2018/043985
§ 371 (c)(1),
(2) Date: Sep. 14, 2020

(87) PCT Pub. No.: WO2019/181073
PCT Pub. Date: Sep. 26, 2019

(65) Prior Publication Data
US 2021/0010796 A1   Jan. 14, 2021

(30) Foreign Application Priority Data

Mar. 23, 2018  (JP) ............................. JP2018-055853

(51) Int. Cl.
*G01B 9/02* (2022.01)
*G01B 9/02091* (2022.01)
(Continued)

(52) U.S. Cl.
CPC ......... *G01B 9/02091* (2013.01); *G01N 21/45* (2013.01); *G01N 33/4833* (2013.01); *A61B 5/0066* (2013.01)

(58) Field of Classification Search
CPC ............... G01B 9/02091; G01N 21/45; G01N 33/4833; G01N 15/1463;
(Continued)

(56) References Cited

U.S. PATENT DOCUMENTS

2007/0076211 A1   4/2007  Toida et al.
2008/0297806 A1*  12/2008  Motaghiannezam ........................
                                                       G01B 9/02028
                                                              356/484
(Continued)

FOREIGN PATENT DOCUMENTS

JP   2007-101249 A   4/2007
JP   2008-175698 A   7/2008
(Continued)

OTHER PUBLICATIONS

International Search Report issued in corresponding International Patent Application No. PCT/JP2018/043985, dated Feb. 19, 2019, with English translation.
(Continued)

*Primary Examiner* — Hwa Andrew Lee
(74) *Attorney, Agent, or Firm* — McDermott Will & Emery LLP (57) ABSTRACT

To optimize an imaging range in a depth direction in terms of a relationship with a resolution, an OCT apparatus includes a signal processor that determines a reflected light intensity distribution of an imaging object on the basis of a spectrum of a detected interference light. The signal processor performs spectrum conversion, having a conversion characteristic with which a light source spectrum is converted to a Gaussian distribution curve, on the spectrum of the interference light, and determines the reflected light intensity distribution by Fourier-transforming a spectrum resulting from the spectrum conversion. In the conversion characteristic, the light source spectrum and the Gaussian
(Continued)

distribution curve have center wavelengths differing from each other.

7 Claims, 8 Drawing Sheets

(51) Int. Cl.
   *G01N 21/45* (2006.01)
   *G01N 33/483* (2006.01)
   *A61B 5/00* (2006.01)
(58) Field of Classification Search
   CPC ... G01N 2015/1454; G01N 2015/1447; G01N 2015/1006; G01N 15/1429; G01N 2015/1445; G01N 15/1434; G01N 21/4795; A61B 5/0066
   See application file for complete search history.

(56) References Cited

U.S. PATENT DOCUMENTS

| | | | |
|---|---|---|---|
| 2010/0150467 A1 | 6/2010 | Zhao et al. | |
| 2011/0026035 A1 | 2/2011 | Muto et al. | |
| 2011/0267583 A1* | 11/2011 | Hayashi | G01B 9/02044 356/479 |
| 2013/0135614 A1 | 5/2013 | Wax et al. | |
| 2014/0016136 A1 | 1/2014 | Kawano et al. | |
| 2015/0285685 A1* | 10/2015 | Wax | G01J 3/0218 356/456 |

FOREIGN PATENT DOCUMENTS

| | | |
|---|---|---|
| JP | 2011-024842 A | 2/2011 |
| JP | 2013-518256 A | 5/2013 |
| JP | 2016-188795 A | 11/2016 |
| WO | 2012/128367 A1 | 9/2012 |

OTHER PUBLICATIONS

Hendargo, et al. "Synthetic wavelength based phase unwrapping in spectral domain optical coherence tomography," Optics Express, 2009, vol. 17, Issue 7, pp. 5039-5051.

Japanese Decision to Grant Patent issued in corresponding Japanese Patent Application No. 2018-055853, dated Jul. 12, 2022, with English translation.

H.C. Hendargo et al., "Synthetic Wavelength-Based Phase Unwrapping in Fourier Domain Optical Coherence Tomography", Proc of SPIE, vol. 7168, 2009, pp. 1-4.

R.A. Leitgeb et al., "Spectroscopic Fourier Domain Optical Coherence Tomography: Principle, Limitations, and Applications", Proc of SPIE, vol. 5690, 2005, pp. 151-158.

Extended European Search Report issued in corresponding European Patent Application No. 18910562.0-1020, dated Oct. 22, 2021.

* cited by examiner

OPTICAL COHERENCE TOMOGRAPHIC APPARATUS AND OPTICAL COHERENCE TOMOGRAPHIC METHOD PERFORMING SPECTRUM CONVERSION BASED ON SINGLE GAUSSIAN DISTRIBUTION CURVE

CROSS REFERENCE TO RELATED APPLICATIONS

This application is the U.S. National Phase under 35 U.S.C. § 371 of International Application No. PCT/JP2018/043985, filed on Nov. 29, 2018, which claims the benefit of Japanese Application No. 2018-055853, filed on Mar. 23, 2018, the entire contents of each are hereby incorporated by reference.

TECHNICAL FIELD

The present invention relates to a tomographic technique based on the principles of optical coherence tomographic imaging.

BACKGROUND ART

In technical fields of medical science and biochemistry, cells or microorganisms cultured in a container are observed. Techniques of imaging cells and the like to be observed using a microscope, for example, have been suggested as methods of observing such cells without affecting the cells. One of these techniques utilizes optical coherence tomography (hereinafter abbreviated as "OCT") techniques. These OCT techniques include a technique called Fourier domain optical coherence tomography (hereinafter abbreviated as "FD-OCT") by which light containing various types of wavelength components and emitted from a light source is caused to enter an imaging object, and interference light occurring between light reflected from the imaging object and reference light is detected. The spectrum of the interference light is Fourier-transformed to acquire information about the imaging object in a depth direction. If the imaging object is a living body or a cell cultured in a culture solution, for example, a light source to be generally used has a spectrum centered on a near-infrared region.

According to the FD-OCT technique, if the spectrum of a light source differs from a Gaussian distribution, a side lobe appearing in a spectrum resulting from Fourier transform is known to cause image noise. To handle this problem, according to a technique disclosed in PTL 1, for example, reduction in a side lobe is encouraged by converting the spectrum of an interference signal in such a manner that the envelop of a light source spectrum follows a Gaussian distribution form at the time of detection of the spectrum, and then by performing Fourier transform on the resultant spectrum.

A different FD-OCT imaging apparatus is disclosed in PTL 2, for example. The apparatus disclosed in PTL 2 changes a definition (resolution) in a horizontal direction (a direction vertical to the optical axis of an objective optical system) by changing the numerical aperture (NA) of the objective optical system, thereby switching between a high-definition mode and a low-definition mode.

CITATION LIST

Patent Literature

[PTL 1] JP2007-101249A
[PTL 2] JP2011-024842A

SUMMARY

Technical Problem

According to the FD-OCT imaging, a resolution in a depth direction depends on the spectrum of light emitted from a light source to enter an imaging object, as will be described in detail later. More specifically, to obtain a high resolution, a shorter center wavelength and a wider light source spectrum are desirable. With attention on the scattering characteristic of light, however, a longer wavelength results in less scattering to cause the light to reach a depth of the imaging object, thereby extending an imaging possible range in the depth direction. In this way, a resolution and an imaging possible range in the depth direction are in a trade-off relationship with each other in terms of the wavelength of the light source, and are desirably balanced appropriately in an imaging condition to be applied. However, a consideration has conventionally been given to an imaging condition paying attention mainly to a resolution, and a viewpoint of positively controlling an imaging possible range is missing. In particular, in an apparatus such as that disclosed in patent literature 2 that makes a resolution changeable by switching between optical systems, while switching between the optical systems changes an imaging possible range in a horizontal direction, an imaging possible range in the depth direction remains constant. For this reason, it cannot be said that an optimum imaging condition is provided in each of the high-definition mode and the low-definition mode. From these viewpoints, the conventional techniques described above are susceptible to improvement in terms of optimizing an imaging possible range while achieving a favorable resolution.

Solution to Problem

The present invention has been made in view of the foregoing problem. In an imaging technique employing optical coherence tomography, an object of the present invention is to provide a technique allowing optimization of an imaging possible range in the depth direction in terms of a relationship with a resolution.

To attain the foregoing object, an aspect of an optical coherence tomographic apparatus according to the present invention includes: a light source that emits light having a light source spectrum with a plurality of wavelength components; an interference light generator that branches the light from the light source, causes one branch light to enter an imaging object via an objective lens, collects light reflected from the imaging object with the objective lens, and couples the collected light to different branch light, thereby generating interference light; a detector that detects the interference light; and a signal processor that determines a reflected light intensity distribution of the imaging object on the basis of the spectrum of the detected interference light, wherein the signal processor performs spectrum conversion, having a conversion characteristic with which the light source spectrum is converted to a Gaussian distribution curve, on the spectrum of the interference light, and determines the reflected light intensity distribution by Fourier-transforming a spectrum resulting from the spectrum conversion, and in the conversion characteristic, the light source spectrum and the Gaussian distribution curve have center wavelengths differing from each other.

To attain the foregoing object, an aspect of an optical coherence tomographic method, comprising: a step of branching light having a light source spectrum with a plurality of wavelength components, causing one branch light to enter an imaging object via an objective lens, collecting light reflected from the imaging object with the objective lens, and coupling the collected light to different branch light, thereby generating interference light; and a step of detecting the interference light and determining a reflected light intensity distribution of the imaging object on the basis of the spectrum of the detected interference light, wherein spectrum conversion, having a conversion characteristic with which the light source spectrum is converted to a Gaussian distribution curve, is performed on the spectrum of the interference light, a spectrum resulting from the spectrum conversion is Fourier-transformed to determine the reflected light intensity distribution, and in the conversion characteristic, the light source spectrum and the Gaussian distribution curve have center wavelengths differing from each other.

According to the invention having the foregoing configuration, in Fourier domain optical coherence tomography (FD-OCT imaging), reduction in noise due to a side lobe is encouraged by performing the spectrum conversion on the spectrum of the interference light. This achieves acquisition of a tomographic image of favorable image quality. A resolution in a depth direction in the FD-OCT imaging, namely, a resolution in a direction along the optical axis of the objective lens becomes higher as the center wavelength of the light source spectrum becomes shorter and the spectrum width of the light source spectrum becomes larger.

In the FD-OCT imaging involving the spectrum conversion, both the center wavelength and spectrum width of the light source spectrum involved in a resolution in the depth direction are values resulting from the spectrum conversion. Further, an imaging possible range in the depth direction in a tomographic image obtained from a result of Fourier transform depends on a degree of content of a long wavelength component after the spectrum conversion. For these reasons, a resolution and an imaging possible range in the depth direction are controllable using a conversion characteristic for the spectrum conversion.

On the other hand, a resolution in a horizontal direction perpendicular to the optical axis of the objective lens is proportional to the center wavelength of the light source spectrum and is inversely proportional to the numerical aperture of the objective lens. In this case, the light source spectrum is the spectrum of light actually passing through the objective lens. Namely, this is the spectrum of light emitted from the light source itself and is not the one resulting from the spectrum conversion. Further, with a substantially equal lens diameter, increase in numerical aperture increases a resolution while narrowing an imaging possible range.

According to the conventional techniques, a light source in a wide band having a short center wavelength is selected for the purpose of obtaining a higher resolution. To use the spectrum width of this light source effectively, spectrum conversion is performed on the basis of a Gaussian distribution curve having a center wavelength matching the center wavelength of the light source spectrum. In terms of the purpose of the FD-OCT imaging to acquire a tomographic image or a three-dimensional image of an imaging object, however, it is not required in many cases to increase only one of a resolution in the depth direction and a resolution in the horizontal direction determined by the light source spectrum and the numerical aperture of the objective lens. These resolutions can actually be substantially equal to each other.

From this viewpoint, a conversion characteristic for the spectrum conversion may be manipulated for the purpose of optimizing a resolution and an imaging possible range in the depth direction. More specifically, a resolution and an imaging possible range in the depth direction become adjustable by manipulating the center wavelength of a Gaussian distribution curve representing the conversion characteristic. For example, setting the center wavelength of the Gaussian distribution curve at a shorter wavelength than the center wavelength of the light source spectrum improves a resolution in the depth direction while narrowing an imaging possible range. Conversely, setting the center wavelength of the Gaussian distribution curve at a longer wavelength than the center wavelength of the light source spectrum extends an imaging possible range while reducing a resolution in the depth direction.

As described above, shifting the center wavelength of the Gaussian distribution curve depending on the spectrum conversion characteristic toward a shorter wavelength or toward a longer wavelength than the center wavelength of the light source spectrum attains a balance between a resolution and an imaging possible range in the depth direction, as well as simply encouraging a higher resolution. This allows an imaging possible range in the depth direction to be optimized in terms of a relationship with a resolution in the same direction.

Advantageous Effects of Invention

As described above, according to the present invention, in an imaging technique employing optical coherence tomography, the center wavelength of a Gaussian distribution curve during spectrum conversion is shifted from the center wavelength of a light source spectrum. This achieves an optimum balance between a resolution and an imaging possible range in the depth direction.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF EMBODIMENTS

Figure 1:
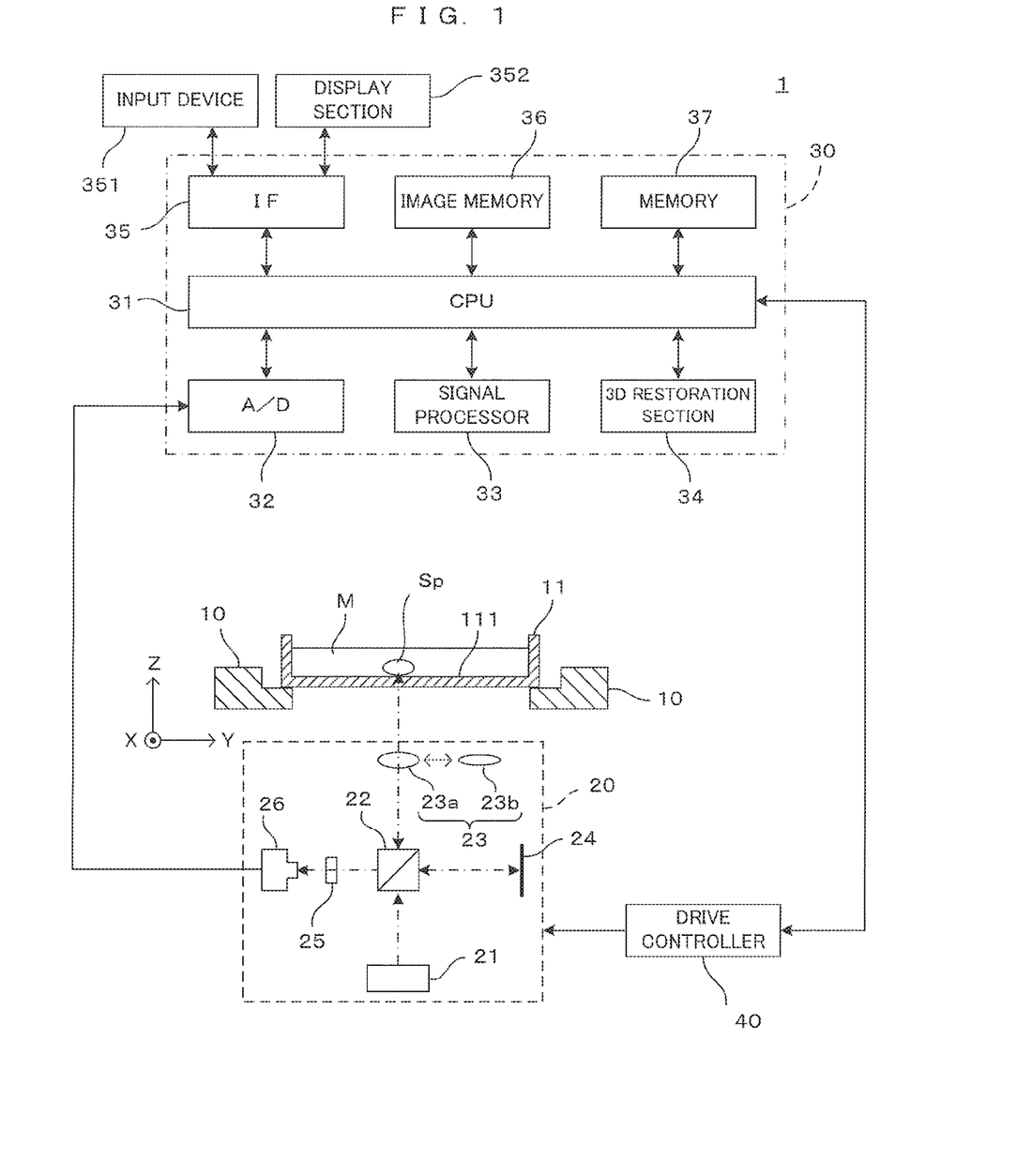
FIG. 1 is a drawing showing an embodiment of an imaging apparatus according to the present invention.

FIG. 1 is a drawing showing an embodiment of an imaging apparatus according to the present invention. The imaging apparatus 1 tomographically images a cell cultured in a culture medium M, a spheroid (cell aggregate) which consists of many cells, an organ-like structure (hereinafter, referred to as a "cell or the like" generically) as an imaging object, processes the obtained tomographic image and generates a stereoscopic image of the imaging object. Note that although an example of imaging a spheroid in the culture medium as the imaging object is illustrated here, the imaging object is not limited to this. For unified presentation of the directions in drawings, the XYZ orthogonal coordinate axes are established as shown in FIG. 1. The XY plane is a horizontal surface. The Z axis represents the vertical axis, in more detail, the (−Z) direction represents the vertically downward direction.

The imaging apparatus 1 comprises a holder 10. The holder 10 holds in an approximately horizontal posture a shall plate-like container 11 having a flat bottom surface made of transparent and uniform glass or resin and called a "dish" in such a manner that its opening is directed toward above. The container 11 has a flat bottom surface made of transparent and uniform glass or resin and is called a "dish". A predetermined amount of an appropriate culture medium M is poured in the container 11 in advance, and a sample Sp is cultured in the medium at the bottom part 111 of the container 11. Although FIG. 1 shows only one sample Sp, a plurality of spheroids Sp may be cultured in one container 11.

An imaging unit 20 is disposed below the container 11 which is held by the holder 10. An optical coherence tomography (OCT) apparatus capable of imaging tomographic images of an imaging object in a non-contact and non-destructive (non-invasive) manner is used as the imaging unit 20. As described in detail later, the imaging unit 20 which is an OCT apparatus comprises a light source 21 which emits illumination light for an imaging object, a beam splitter 22, an objective optical system 23, a reference mirror 24, a spectroscope 25, a photo-detector 26 and a shutter 27.

Further, the imaging apparatus 1 comprises a control unit 30 which controls operations of the apparatus and a drive controller 40 which controls movement of movable parts of the imaging unit 20. The control unit 30 comprises a CPU (Central Processing Unit) 31, an A/D convertor 32, a signal processor 33, a 3D restoration section 34, an interface (IF) section 35, an image memory 36 and a memory 37.

The CPU 31 governs operations of the entire apparatus by executing a predetermined control program. The control program executed by the CPU 31 and data which are generated during processing are saved in the memory 37. The A/D convertor 32 converts a signal which the photo-detector 26 of the imaging unit 20 outputs in accordance with the amount of received light into digital image data. The signal processor 33 performs image processing described later based upon a digital data outputted from the A/D converter 32, thereby generates a tomographic image of the imaging object. Based upon image data of a plurality of tomographic images, the 3D restoration section 34 generates a stereoscopic image (3D image) of the imaged cell aggregate. The image memory 36 saves the image data of the tomographic images generated by the signal processor 33 and the image data of the stereoscopic image generated by the 3D restoration section 34.

The interface section 35 realizes communication between the image processing apparatus 1 and outside. More specifically, the interface section 35 has a function of communicating with external equipment, and a user interface function of accepting manipulation by a user and informing the user of various types of information. For receiving an instruction input, the interface section 35 comprises an input device 351, for instance a key board, a mouse, a touch panel or the like which can accept manipulation and entry concerning selection of the functions of the apparatus, setting of operating conditions, etc. Further, for informing to the user, a display section 352 which is a liquid crystal display for example and shows various types of processing results such as the tomographic images imaged by the imaging unit 20 and the three-dimensional image generated by the 3D restoration section 34 is connected to the interface section 35.

Further, the CPU 31 sends a control command to the drive controller 40, and the drive controller 40 makes the movable parts of the imaging unit 20 execute predetermined operation in accordance with the control command. As described next, the tomographic images of the spheroid (cell aggregate) which is the imaging object are obtained owing to combination of scan moving of the imaging unit 20 executed by the drive controller 40 and detection of the amount of the received light by the photo-detector 26.

Figure 2A:
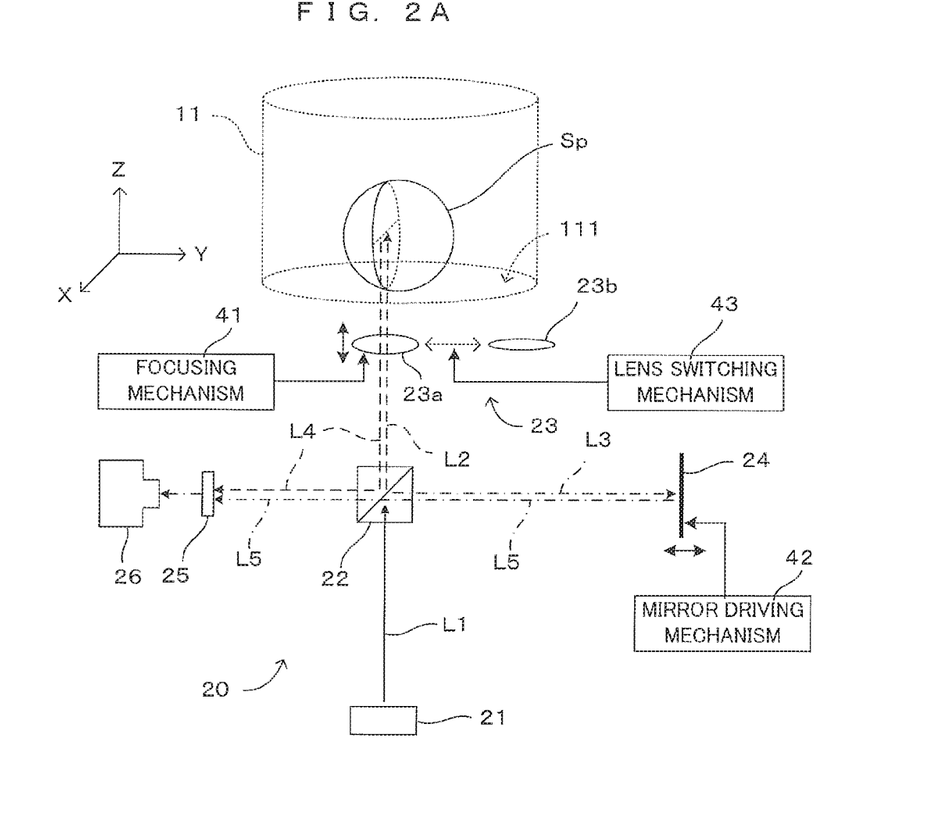
FIG. 2A is a first drawing for describing the principle of imaging in this imaging apparatus.
Figure 2B:
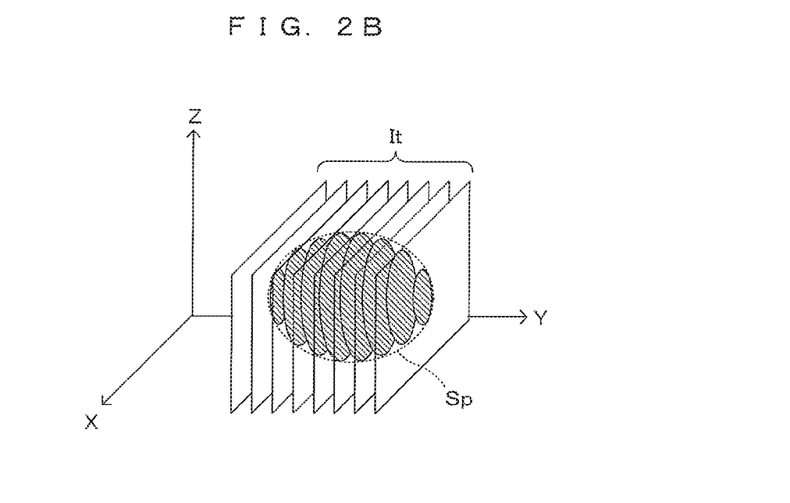
FIG. 2B is a second drawing for describing the principle of imaging in this imaging apparatus.

FIGS. 2A and 2B are drawings for describing the principle of imaging in this imaging apparatus. More specifically, FIG. 2A is a drawing which shows optical paths inside the imaging unit 20, and FIG. 2B is a schematic drawing which shows tomographic imaging of a spheroid. As described earlier, the imaging unit 20 works as an optical coherence tomography (OCT) apparatus. Although the spheroid Sp is described in a roughly spherical shape for illustration purposes, the shape of the sample Sp actually imaged is not particularly limited.

In the imaging unit 20, from the light source 21 which includes a light emitting element such as a light emitting diode or a super luminescent diode (SLD) for instance, a low-coherence light beam L1 containing a wide-range wavelength components is emitted. The light beam L1 impinges upon the beam splitter 22. Some light L2 indicated by the broken-line arrow propagates toward the well W, and some light L3 indicated by the arrow of long dashed short dashed line propagates toward the reference mirror 24.

The light L2 propagating toward the container 11 is incident on the container 11 by way of the objective optical system 23. More specifically, the light L2 emitted from the beam splitter 22 is incident on the bottom part 111 of the container 11 via the objective optical system 23. The objective optical system 23 has a function of converging the light L2 propagating from the beam splitter 22 toward the container 11 to the imaging object in the container 11 (sample Sp in this case) and a function of collecting the reflected light emitted from the imaging object and causing it to propagate toward the beam splitter 22. Although the objective optical system 23 is illustrated as a single objective lens in FIG. 2A, the objective optical system 23 may include a plurality of optical elements.

The imaging apparatus 1 includes two types of objective lenses 23a, 23b having mutually different numerical apertures and a lens switching mechanism 43 provided in the drive controller 40. The lens switching mechanism 43 changes these two types of objective lenses 23a, 23b to selectively position on the optical path of the light L2. For switching between a high-magnification imaging having a high-definition and a narrow imaging range and a low-magnification imaging having a lower-definition and a wide imaging range, for example, such a switching mechanism can be used. Here, one objective lens 23a have a numerical aperture large than that of the other objective lens 23b. The objective lens 23a is used in the high-magnification imaging, while the objective lens 23b is used in the low-magnification imaging. When the two types of objective lenses 23a and 23b are not particularly distinguished, they are described as "objective lens 23" in this specification.

The objective optical system 23 is movable in the Z direction by a focusing mechanism 41 which is disposed to the drive controller 40. This enables the focus position of the objective optical system 23 with respect to the imaging object to be changed in the Z direction. An optical axis of the objective optical system 23 is parallel to a vertical direction and, therefore, perpendicular to the bottom part 111 of the container 11 in the form of a flat plate. Further, an incident direction of illumination light on the objective optical system 23 is parallel to the optical axis. The arrangement of the objective optical system 23 is determined such that a light center of the light coincides with the optical axis.

The incident light L2 via the bottom part 111 is reflected at the surface of the sample Sp unless the sample Sp transmits the light beam L2. On the other hand, when the sample Sp has a property of transmitting the light beam L2 to a certain extent, the light beam L2 propagates into inside the sample Sp and is reflected by a structure element which is inside the spheroid. When the near infrared rays for instance are used as the light beam L2, it is possible to allow the incident light to reach even inside the sample Sp. The reflected light from the sample Sp is irradiated as scattered light in various directions. Out of that, light L4 irradiated within a light collection range of the objective optical system 23 is collected by the objective optical system 23 and sent to the beam splitter 22.

The reference mirror 24 is supported movably by a mirror driving mechanism 42 provided in the drive controller 40 so that the reference mirror 24 is movable in a direction (Y direction in FIG. 2A) along the incident direction while a reflection surface thereof is perpendicular to an incident direction of the light L3. The light L3 incident on the reference mirror 24 is reflected by the reflection surface and propagates toward the beam splitter 22 as light L5 propagating in an opposite direction along an incident optical path. This light L5 becomes reference light. By changing the position of the reference mirror 24 by the mirror driving mechanism 42, an optical path length of the reference light changes. The position of the reference mirror 24 is changed not only automatically in accordance with a purpose of the imaging, but arbitrarily by the setting input from the user via the input device 351.

The reflected light L4 reflected by a surface or an internal reflecting surface of the sample Sp and reference light L5 reflected by the reference mirror 24 are incident on the photo-detector 26 via the beam splitter 22. At this time, interference due to a phase difference between the reflected light L4 and the reference light L5 occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the beam splitter 22 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier-transforming the interference signal output from the photo-detector 26 according to the interference light detected by the photo-detector 26, the reflected light intensity distribution of the sample Sp in the depth direction, i.e. in the Z direction at the incident position of the light beam L2 is obtained. By scanning the light beam L2 incident on the container 11 in the X direction, the reflected light intensity distribution in a plane parallel to an XZ plane is obtained, with the result that a tomographic image of the sample Sp having this plane as a cross-section can be generated. In this specification, a series of operations for obtaining one tomographic image It in a cross-section parallel to the XZ plane by beam scanning in the X direction is referred to as one imaging.

Images are obtained by changing the incident position of the light L2 along the Y direction over multiple steps and imaging a tomographic image for every change. As shown in FIG. 2B, a number of tomographic images It of the sample Sp are obtained along cross-sectional surfaces which are parallel to the XZ plane. As the scan pitch in the Y direction is reduced, it is possible to obtain image data with sufficient resolution to grasp the stereoscopic structure of the sample Sp. Scan movements of the light beam in X and Y direction are realized as an optical device (not shown) changing an optical path such as a Galvanometer mirror changes the incident position of the light beam to X and Y direction, the container 11 carrying the sample Sp and imaging unit 20 relatively move to X and Y direction or the like.

Note that, in the imaging unit 20 of the above description, it is the beam splitter 22 that has a function of dividing the light from the light source 21 to the illumination light and the reference light and a function of mixing the signal light and the reference light to cause interference. On the other hand, some of OCT imaging apparatuses are known to have a dividing/mixing function, for example, an optical fiber coupler as described below.

Figure 3A:
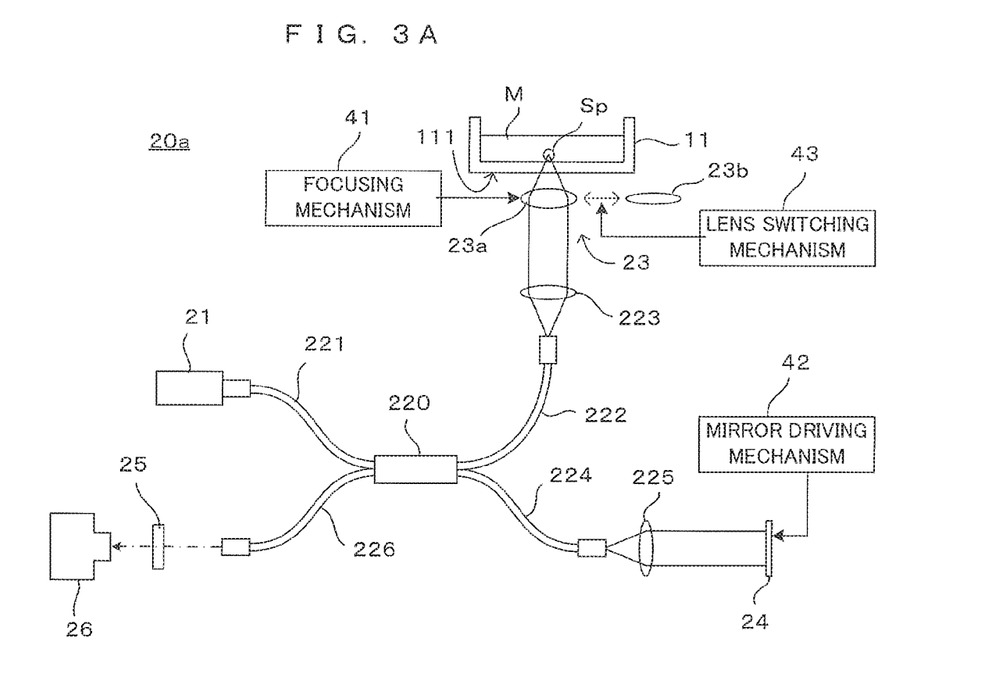
FIG. 3A is a first diagram showing a configuration example of the OCT apparatus.
Figure 3B:
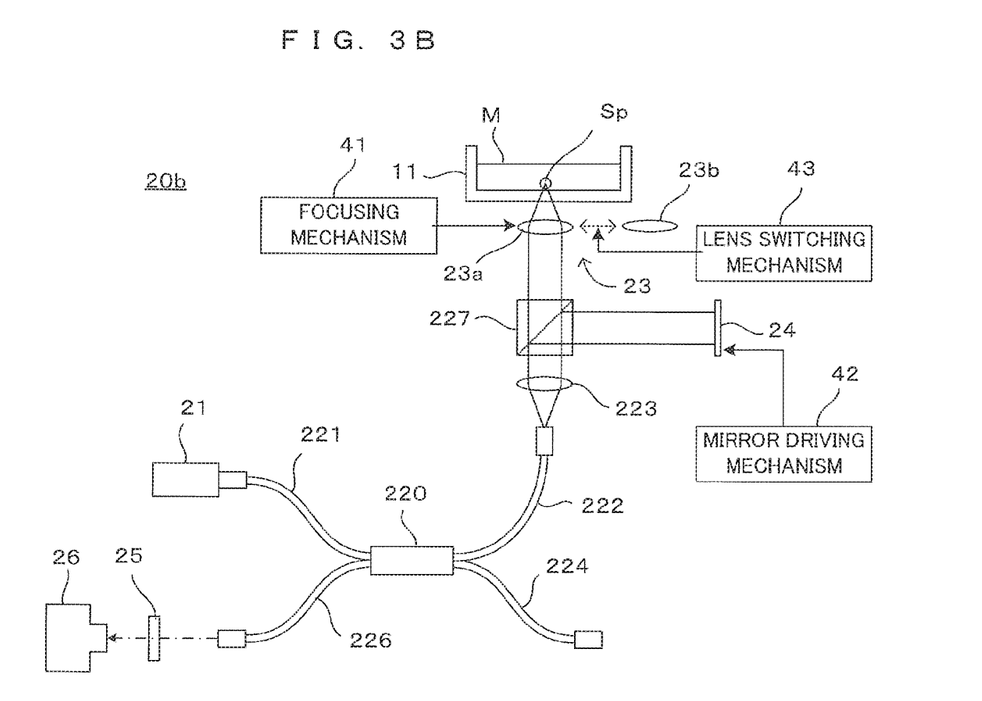
FIG. 3B is a second diagram showing the configuration example of the OCT apparatus.

FIGS. 3A and 3B are diagrams showing other configuration examples of the OCT apparatus. Note that, in the following description, constituent components same as or corresponding to those of other embodiments are denoted by the same reference signs to facilitate understanding. The structures and functions thereof are basically the same as those of the embodiment unless particularly described, and thereby the detail description is omitted. An OCT imaging principle for detecting interference light by the optical fiber coupler is not described in detail since it is same as the above embodiment.

In an example shown in FIG. 3A, an imaging unit 20a includes an optical fiber coupler 220 instead of the beam splitter 22 as a dividing/mixing optical device. One 221 of optical fibers constituting the optical fiber coupler 220 is connected to a light source 21 and low-coherence light emitted from the light source 21 is branched into lights to two optical fibers 222, 224 by the optical fiber coupler 220. The optical fiber 222 constitutes an object side optical path. More specifically, light emitted from an end part of the optical fiber 222 is incident on an objective optical system 23 via a collimator lens 223. Reflected light (signal light) from an imaging object is incident on the optical fiber 222 via the objective optical system 23 and the collimator lens 223.

Another optical fiber 224 constitutes a reference side optical path. More specifically, light emitted from an end part of the optical fiber 224 is incident on a reference mirror 24 via a collimator lens 225. Reflected light (reference light) from the reference mirror 24 is incident on the optical fiber 224 via the collimator lens 225. The signal light propagating in the optical fiber 222 and the reference light propagating in the optical fiber 224 interfere in the optical fiber coupler 220. The interference light is incident on a photo-detector 26 via an optical fiber 226 and a spectroscope 25. An intensity distribution of the reflected light on the imaging object is obtained from the interference light received from the photo-detector 26 as in the above principle.

Also in an example shown in FIG. 3B, an optical fiber coupler 220 is provided in an imaging unit 20b. However, an optical fiber 224 is not used and a collimator lens 223 and a beam splitter 227 as an optical device are provided on an optical path of light emitted from an optical fiber 222. As the principle described above, an objective optical system 23 and a reference mirror 24 are arranged on two optical paths branched by the beam splitter 227. In such a configuration, signal light and reference light are mixed by the beam splitter 227 and interference light generated thereby is guided to a photo-detector 26 through the optical fibers 222, 226.

In these examples, the optical path of each light propagating in a space is partially replaced by an optical fiber in the principle diagram of FIG. 2A, but the operation principle is the same. Also in these examples, the focusing mechanism 41 moves the objective optical system 23 in directions toward and away from the container 11, whereby a focal depth of an objective optical system 23 with respect to the imaging object can be adjusted. The lens switching mechanism 43 can change the two types of objective lenses 23a, 23b. Further, the mirror driving mechanism 42 moves the reference mirror 24 along the incident direction of the light, whereby the optical path length of the reference light can be changed.

Figure 4:
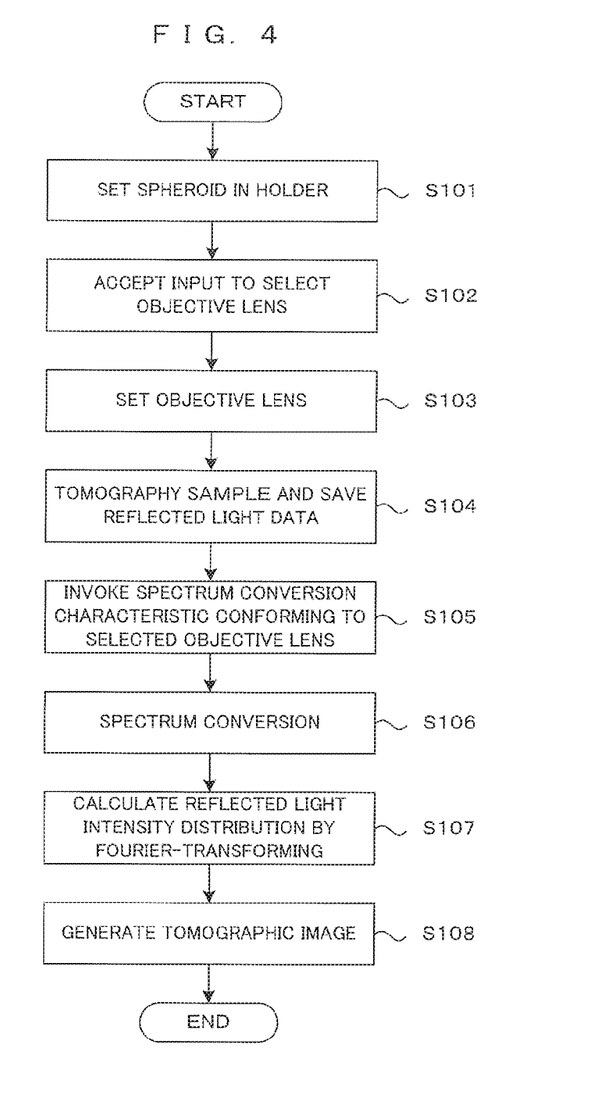
FIG. 4 is a flowchart showing the operation of the image processing apparatus.

FIG. 4 is a flowchart showing the operation of the image processing apparatus. First, the container 11 carrying the sample Sp to be imaged and a culture solution together is set in the holder 10 by a user or a transport robot (step S101). Further, an input from the user to select the objective lens 23 is accepted through the input device 351 (step S102). Namely, an input is accepted from the user indicating which one of the high-magnification imaging using the objective lens 23a having a large numerical aperture and the low-magnification imaging using the objective lens 23b having a small numerical aperture is desired by the user.

The CPU 31 controls the imaging unit 20 and the drive controller 40 to tomographically image the sample Sp as an imaging object in the container 11. More specifically, the lens switching mechanism 43 arranges one of the two types of objective lens 23a and 23b designated by the input for selection from the user on an optical path of the light beam L2 (step S103). The imaging unit 20 performs tomography based on the principles described above. Data about reflected light is obtained from the intensity of interference light in each wavelength output from the photo-detector 26. The reflected light data is saved into the image memory 36 or the memory 37 (step S104).

The signal processor 33 invokes a spectrum conversion characteristic conforming to the selected objective lens from several types of spectrum conversion characteristics stored in advance in the memory 37 (step S105), and performs spectrum conversion on the basis of the invoked conversion characteristic (step S106). A spectrum resulting from the conversion is Fourier-transformed to calculate a reflected light intensity distribution at each position in the depth direction (step S107). Then, the signal processor 33 generates a tomographic image indicating a tomographic image in the well W at one cross-section parallel to the XZ plane from a reflected light intensity distribution at each position in the X direction (step S108). Tomographic image data is generated in the same way at each position in the Y direction. The generated tomographic image data is saved in the image memory 36, and is displayed on the display section 352 or delivered to the outside, if necessary.

The 3D restoration section 34 can generate 3D image data corresponding to a stereoscopic image of the sample Sp on the basis of the tomographic image data acquired in this way. As a more specific example, the 3D restoration section 34 can obtain 3D image data through interpolation in the Y direction on tomographic image data acquired discretely in the Y direction. As a technique of generating 3D image data from tomographic image data has already been put to practical use, it will not be described in detail.

Next, the conversion characteristic for the spectrum conversion in step S106 will be described in more detail. While specific principles of the spectrum conversion will not be described herein, the spectrum conversion is performed for the purpose of reducing image noise resulting from the presence of a distribution having a non-Gaussian form in a light source spectrum in a wide band. Specifically, the spectrum of interference light is converted by applying a conversion characteristic such that the spectrum of the light L1 emitted from the light source is converted to a Gaussian distribution form. This makes it possible to reduce a side lobe to occur in each wavelength component in reflected light, as if the illumination light L2 entering the sample Sp as an imaging object had a spectrum of a Gaussian distribution form.

Figure 5A:
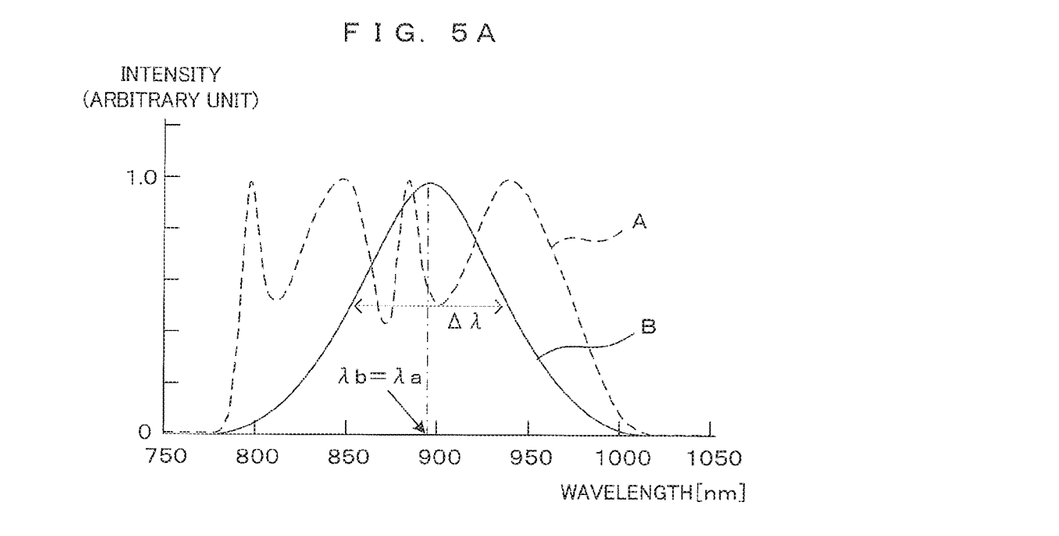
FIG. 5A shows a first example of spectrum conversion characteristic.
Figure 5B:
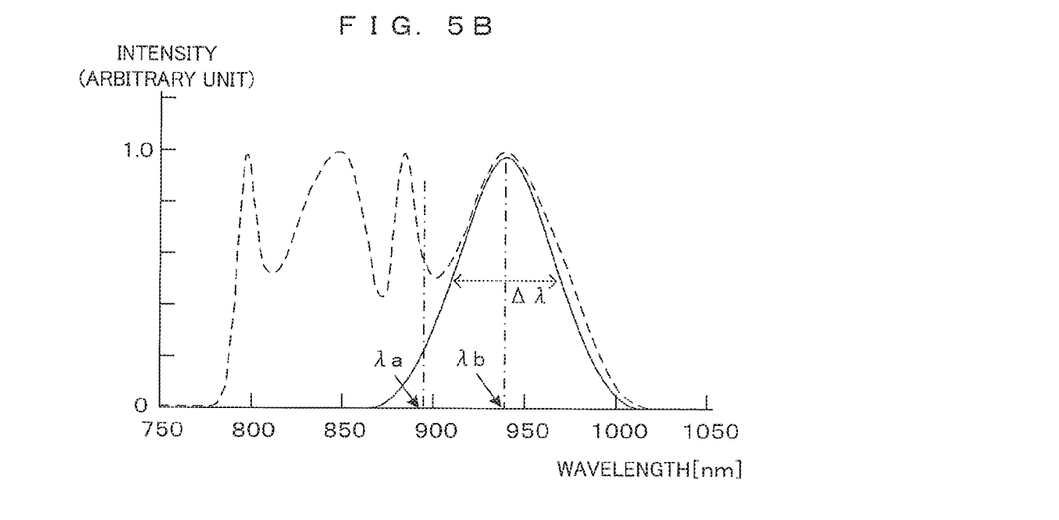
FIG. 5B shows a second example of spectrum conversion characteristic.

FIGS. 5A and 5B show examples of spectrum conversion characteristics. FIG. 5A shows an example where there is a match in a center wavelength between the spectrum of a light source and a Gaussian distribution curve depending on a conversion characteristic. In FIG. 5A, a dashed curve A shows an example of the light source spectrum of the light L1 emitted from the SLD as an example of the light source 21. The center wavelength of this spectrum is expressed by a sign λa. A solid curve B shows a virtual light source spectrum resulting from the conversion and is a Gaussian distribution curve with a center wavelength λb. Here, λb equals to λa as the center wavelength λb is matched with the center wavelength λa of the light source spectrum. What is important in the spectrum conversion is a spectrum shape, namely, intensities of wavelength components relative to each other. For this reason, a vertical axis is expressed in an arbitrary unit with a maximum intensity of 1.

In order for the light source spectrum shown by the dashed line A to become the Gaussian distribution curve shown by the solid line B, an intensity compression or elongation of each wavelength component is necessary. Compression or elongation ration per wavelength component is called a "conversion characteristic." The spectrum conversion is performed by applying this conversion characteristic to the interference light spectrum.

The light source spectrum resulting from the conversion shown by the solid line B in FIG. 5A is a Gaussian distribution curve with the center wavelength $\lambda b$ and a full width at half maximum $\Delta\lambda$. In this case, a resolution Rz in the depth direction (Z direction) during the FD-OCT imaging is known to be expressed by the following formula:

$$Rz=0.44\lambda b^2/\Delta\lambda \quad \text{(Formula 1)}.$$

This shows that a resolution becomes higher as a numerical value expressed by (Formula 1) becomes smaller. Thus, as the center wavelength $\lambda b$ becomes shorter and a spectrum width becomes larger, a higher resolution is obtained.

If the imaging object is a living body or a cell cultured in a culture solution, for example, light frequently used has a light source spectrum in a near-infrared region of a wavelength from about 700 to about 1400 nm, for example. The reason for this is as follows. Light in a visible region of a shorter wavelength than a near-infrared ray is absorbed much in constituents of a living body including hemoglobin. Light in a far infrared region of a longer wavelength is absorbed more in water. In either case, light does not reach a depth of the imaging object to narrow an imaging possible range in the depth direction. By contrast, the wavelength region described above has high permeability to living bodies or cells and suitably applicable to observation of living bodies. From this viewpoint, this wavelength region is called an "Biological Optical Window (second optical window)."

In this wavelength region, scattering occurs dominantly with little absorption of light by the imaging object. Thus, an imaging possible range in the depth direction depends on the scattering characteristic of the imaging object. In a near-infrared region, scattering tends to be reduced at a longer wavelength. For this reason, light is more likely to reach a depth at a longer wavelength. Thus, utilizing a long wavelength component effectively is desirable for extending an imaging possible range.

On the other hand, during the spectrum conversion performed in such a manner as to convert the light source spectrum to a Gaussian distribution form, a signal component in a wavelength region becomes less effective as this wavelength region gets farther from the center wavelength $\lambda b$. If a spectrum conversion characteristic of a short center wavelength is to be applied in terms of increasing a resolution, a signal component in a wavelength comparatively long in a near-infrared region becomes less likely to be reflected in a resultant image. This results in the loss of information about a depth of the imaging object in the depth direction. In this way, the FD-OCT imaging technique encounters a problem that trying to increase a resolution causes narrowing of an observation possible range in the depth direction.

The "imaging possible range" mentioned in this description is an idea differing from an imaging range determined by the principles of the FD-OCT imaging, namely, differing from a range in the depth direction allowing a reflected light intensity distribution to be acquired collectively through beam projection on one point. The imaging possible range in this sense can be extended by changing a focal position of an objective lens in the depth direction, for example. On the other hand, the imaging possible range mentioned in this description means a range in the depth direction reachable by light incident through the container bottom part 111 and in which the incident light is detectable as reflected light. This constraint results from gradual loss of light to occur by absorption or scattering, and cannot be handled by making an effort in imaging or signal processing.

As shown in FIG. 5B, it is assumed that the center wavelength $\lambda b$ is set at a longer wavelength than the center wavelength $\lambda a$ of the light source spectrum. A resolution in the depth direction of this case expressed by (Formula 1) becomes lower than that obtained in the example of FIG. 5A. However, the resolution of this case contains more long wavelength components to reach a greater depth, so that an imaging possible range in the depth direction is extended. Like in this case, the center wavelength $\lambda b$ in a conversion characteristic for the spectrum conversion may be set appropriately and independently of the center wavelength $\lambda a$ of the light source spectrum. This allows a resolution and an imaging possible range in the depth direction to be balanced properly.

The following describes specific examples of spectrum conversion characteristics according to the embodiment. The image processing apparatus 1 of the embodiment allows the high-magnification imaging and the low-magnification imaging to be performed selectively through switching of the objective lens 23. A resolution Rx in the horizontal direction in which limitation is imposed by the light collecting characteristic of the objective lens 23, namely, in a direction (X direction) perpendicular to the optical axis of the objective lens 23, is expressed by the following formula:

$$Rx=k\cdot\lambda a/NA \quad \text{(Formula 2)}.$$

$$Rx=k\cdot\lambda a/NA \quad \text{(Formula 2)}$$

This shows that a resolution becomes higher as a numerical value expressed by (Formula 2) becomes smaller. In (Formula 2), NA is the numerical aperture of the objective lens 23. Further, k is a coefficient of about 0.6. In a practical sense, k can be set at 0.61. In this case, the wavelength $\lambda a$ is the center wavelength of the light source spectrum. Thus, the resolution Rx in the horizontal direction is determined uniquely by the optical characteristics of the light source 21 and the objective lens 23 independently of a spectrum conversion characteristic. Switching the objective lens 23 changes the resolution Rx. With the objective lens 23a having a large numerical aperture NA, the resultant resolution Rx becomes higher than that obtained by the objective lens 23b having a smaller numerical aperture NA.

As described above, the resolution Rz in the depth direction depends on a spectrum conversion characteristic. This shows that, together with changing the resolution Rx in the horizontal direction by switching the objective lens 23, permitting change in the resolution Rz further in the depth direction allows a spectrum conversion characteristic to be defined more flexibly.

Figure 6:
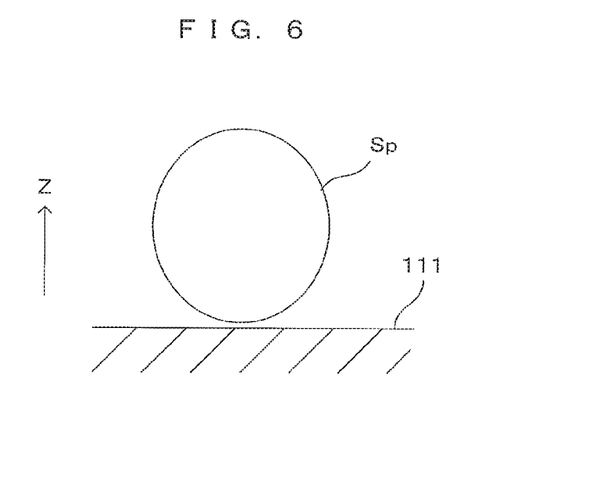
FIG. 6 schematically shows a tomographic image.

FIG. 6 schematically shows a tomographic image. More specifically, FIG. 6 schematically shows an image obtained by tomographically imaging the sample Sp that is a spheroid, for example, through the container bottom part 111 cultured in the culture medium M poured in the container 11. It is assumed that such a tomographic image is obtained by each of the high-magnification imaging using the objective lens 23a and the low-magnification imaging using the objective lens 23b.

Figure 7:
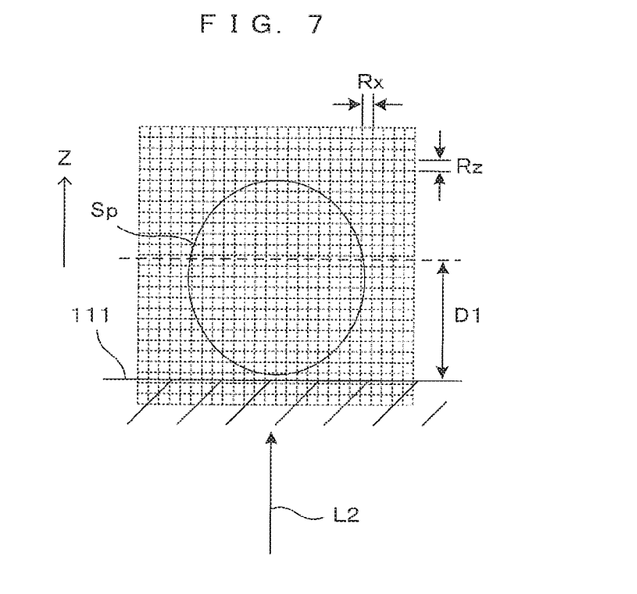
FIG. 7 shows an example of a tomographic image resulting from the high-magnification imaging.

FIG. 7 shows an example of a tomographic image resulting from the high-magnification imaging. A grid indicated by dotted lines in FIG. 7 schematically shows partitions between pixels in the tomographic image. In the high-magnification imaging using the objective lens 23a having a large numerical aperture, a value of the resolution Rx in the horizontal direction perpendicular to an incident direction of the illumination light L2 is smaller than a value obtained by the low-magnification imaging described later.

To obtain equal pixel sizes in the horizontal direction and the depth direction, the resolution Rz in the depth direction expressed by (Formula 1) is required to be substantially equal to the resolution Rx in the horizontal direction. If a high resolution is required in the depth direction, a spectrum conversion characteristic such as that shown in FIG. 5A, for example, is applied effectively in which the center wavelength λb is short and the spectrum width Δλ is large. With the resolution Rx in the horizontal direction of 4 [μm], for example, by applying the conversion characteristic in FIG. 5A in which λb is 898 [nm] and Δλ is 90 [nm] to (Formula 1), Rz is calculated to be nearly equal to 3.9 [μm] to satisfy a required condition.

Light of a long wavelength, which is to reach a depth (in FIG. 7, an upper position) of the sample Sp viewed from the container bottom part 111 for entry of the light beam L2, is lowered relatively by the spectrum conversion. This produces little contribution to a resultant image. As a result, a range in which imaging is substantially possible in the depth direction is limited. The depth of an imaging possible range starting from the container bottom part 111 is expressed by a sign D1.

Figure 8A:
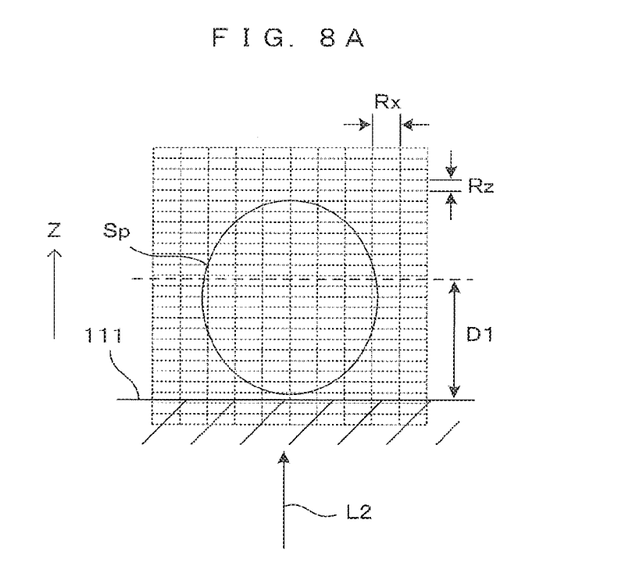
FIG. 8A is a first diagram showing an example of a tomographic image resulting from the low-magnification imaging.
Figure 8B:
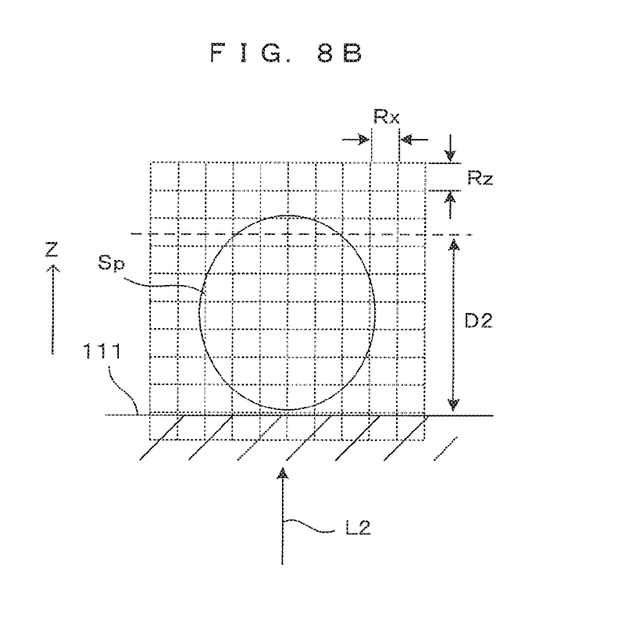
FIG. 8B is a second diagram showing an example of a tomographic image resulting from the low-magnification imaging.

FIGS. 8A and 8B each show an example of a tomographic image resulting from the low-magnification imaging. In the low-magnification imaging using the objective lens 23b having a small numerical aperture, a value of the resolution Rx in the horizontal direction perpendicular to an incident direction of the illumination light L2 is larger than the foregoing value in the high-magnification imaging. The resolution Rx in the horizontal direction in this case is 10 [μm], for example.

If the spectrum conversion characteristic same as that in the high-magnification imaging is applied, the resolution Rz and the imaging possible range D1 in the depth direction remain unchanged, as shown in FIG. 8A. However, as the resolution Rx in the horizontal direction is smaller, the resolution Rz in the depth direction is, in conclusion, excessively higher than the resolution Rx in the horizontal direction.

In this case, a spectrum conversion characteristic such as that in FIG. 5B is introduced in which the center wavelength λb is shifted to a longer wavelength. With the center wavelength λb of 937 [nm] and Δλ of 58 [nm], for example, the resolution Rz in the depth direction is calculated from (Formula 1) to be 6.7 [μm], which is a value closer to the resolution Rx in the horizontal direction. In this case, while a long wavelength component is lost by the conversion characteristic shown in FIG. 5A, such a wavelength component contributes largely to a resultant image. Thus, as shown in FIG. 8B, an imaging possible range D2 in the depth direction becomes wider than the range of the case in FIG. 8A determined by the application of the conversion characteristic in FIG. 5A.

As described above, if the objective lens 23b of a small NA is used, the resolution Rz in the depth direction is permitted to be reduced to a level substantially equal to the resolution Rx in the horizontal direction. By applying a conversion characteristic adapted to this reduction and performing spectrum conversion with this conversion characteristic, it becomes possible to extend an imaging possible range. This feature is also responsive to a need inherent in the low-magnification imaging to observe a wide range without requiring a high resolution.

Figure 9A:
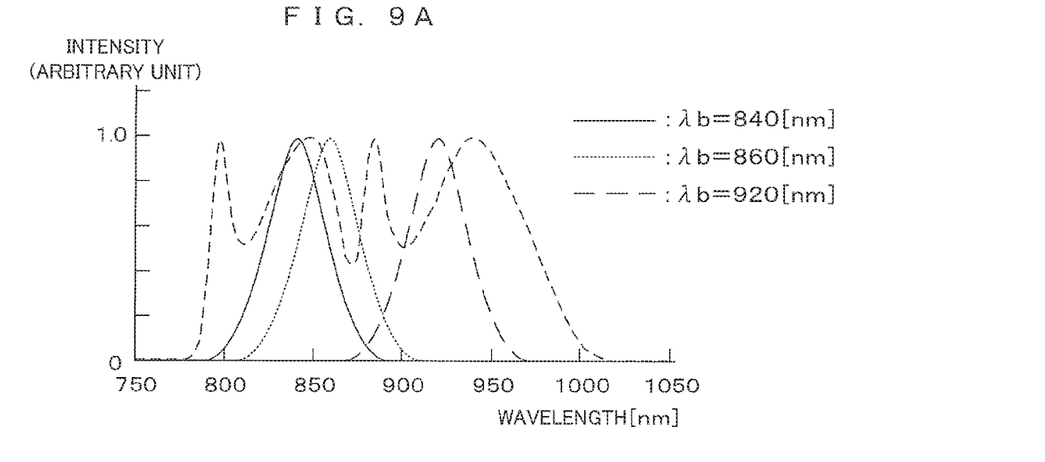
FIG. 9A is a first diagram showing a correspondence between spectrum conversion characteristic and resultant image.
Figure 9B:
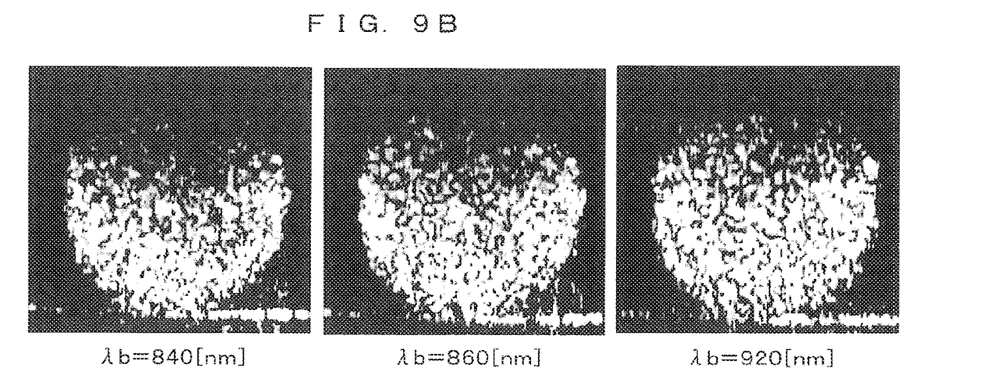
FIG. 9B is a second diagram showing a correspondence between spectrum conversion characteristic and resultant image.
Figure 9C:
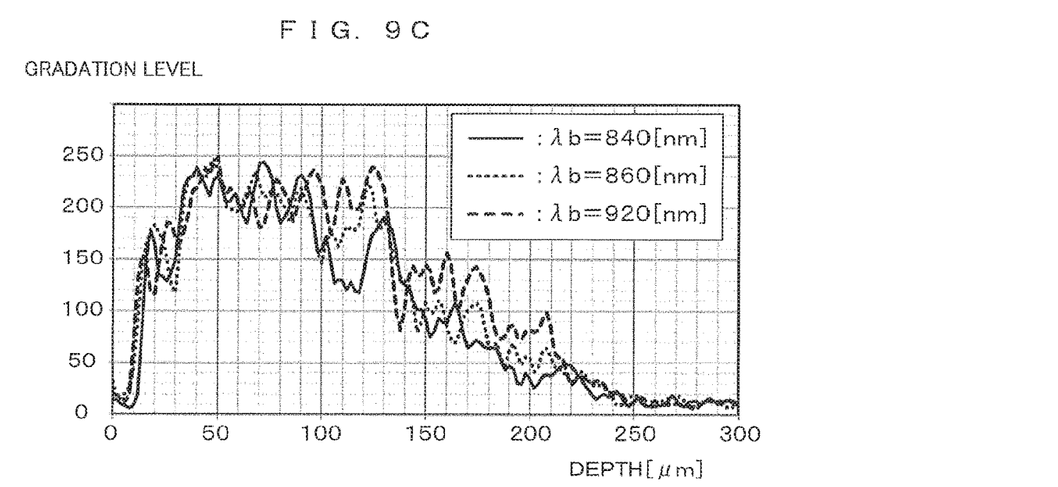
FIG. 9C is a third diagram showing a correspondence between spectrum conversion characteristic and resultant image.

FIGS. 9A to 9C each show correspondences between spectrum conversion characteristics and resultant images. The inventor of the present application conducted an experiment by performing three types of spectrum conversions with the center wavelength λb differing from each other individually on the spectrum of interference light detected by imaging, and then comparing tomographic images expressed by spectra resulting from the conversions. FIGS. 9A to 9C each show exemplary results of the experiment. As shown in FIG. 9A, the performed spectrum conversions have conversion characteristics of making conversions to Gaussian distribution curves with the center wavelength λb of 840 nm, 860 nm, and 920 nm.

FIG. 9B shows examples of tomographic images generated from the spectra resulting from the conversions. These images result from the conversions with λb of 840 [nm], 860 [nm], and 920 [nm] in the order from the left. Comparison between these images shows that a bright region in an upper area of an image is increased as a center wavelength during the spectrum conversion is shifted to a longer wavelength, so that an imaging possible range starting from a lower area of the image is extended.

FIG. 9C shows actually measured result about change in a gradation level occurring in the depth direction (vertical direction) of an image. Concerning a band-like region occupying a central area in the presence of a spheroid image in a lateral direction and extending from the top end to the bottom end of the image in the depth direction in each of the images shown in FIG. 9B, an average pixel value in the lateral direction is plotted along the depth direction. A result of the plot corresponds to FIG. 9C. The depth is defined in an upward direction from the bottom of the image. This plot shows that, as the center wavelength λb of the spectrum conversion becomes longer, bright pixels are present in a deeper region. This shows extension of a range in which reflected light intensity can be reflected in an image, namely, extension of an imaging possible range.

As described above, according to the embodiment, an FD-OCT imaging apparatus performs spectrum conversion process having a conversion characteristic of converting a light source spectrum to a Gaussian distribution form on the spectrum of detected interference light. This reduces the occurrence of image noise due to a side lobe caused in each wavelength component.

A spectrum conversion characteristic is determined not only for the purpose of merely increasing a resolution in the depth direction but also by giving consideration to a balance between a required resolution and a required imaging possible range. More specifically, in the high-magnification imaging using the objective lens 23a having a large numerical aperture, the center frequency wavelength kb in a conversion characteristic is set at the center wavelength λa of a light source spectrum in order to obtain a high resolution using the light source spectrum efficiently. A wide spectrum width is set to be substantially equal to the width of the light source spectrum.

On the other hand, in the low-magnification imaging using the objective lens 23b having a small numerical aperture, a resolution in the depth direction is not required to be the same as a resolution in the high-magnification imaging. For this reason, while reduction in a resolution is permitted, the center wavelength λb in a conversion characteristic is shifted to a longer wavelength, thereby reflecting a component of a longer wavelength contained in light from a light source effectively in an image. This achieves the advantage of extending an effective imaging possible range in the depth direction.

As described above, the imaging apparatus 1 of the above embodiment functions as an "optical coherence tomographic apparatus" of the present invention. The imaging unit 20, 20a and 20b also have the functions of "light source", "interference light generator" and "objective lens" of the present invention. More specifically, the light source 21 and the objective lens 23 respectively correspond to a "light source" and an "interference light generator" of the present invention. The spectroscope 25 and the photo-detector 26 correspond to a "detector" of the present invention. Other optical elements provided in the imaging units 20, 20a, 20b form the "interference light generator" of the present invention.

In the above embodiments, the control unit, particularly the signal processor 33 functions as the "signal processor" of the present invention. A plurality of lenses 23a and 23b correspond to a "a plurality of lenses" of the present invention, and the lens switching mechanism 43 functions as a "switcher" of the present invention.

The present invention is not limited to the foregoing embodiment but various changes other than those described above can be made without departing from the gist of the invention. For example, in the foregoing embodiment, switch is made between the two types of objective lens 23a and 23b having numerical apertures differing from each other. Alternatively, switch may be made between objective lenses of three types of more. In this case, a spectrum conversion characteristic corresponding to each of the objective lenses is set in such a manner that a center wavelength is defined at a shorter wavelength for an objective lens having a larger numerical aperture. This makes it possible to provide a maximum imaging possible range in the depth direction while achieving a resolution in the depth direction suitable for a resolution in the horizontal direction of each objective lens.

In the foregoing embodiment, the center wavelength λb in a spectrum conversion characteristic is set at the same wavelength as the center wavelength λa of a light source spectrum or at a longer wavelength. Alternatively, the center wavelength λb in a spectrum conversion characteristic is settable at a shorter wavelength than the center wavelength λa of the light source spectrum. This encourages further improvement of a resolution while narrowing an imaging possible range in the depth direction.

The image processing apparatus 1 of the foregoing embodiment includes both the imaging function and the signal processing function. Signal processing, which corresponds to one of these functions, can be performed in a general-purpose computer device without an imaging function, for example. For this reason, imaging and signal processing may be performed by different devices.

In particular, by performing imaging once and saving data about interference light before spectrum conversion, it becomes possible to perform spectrum conversions thereafter having various types of conversion characteristics using the saved data and to generate a tomographic image responsive to a purpose. Such a process is preferably executable at a computer device having a general configuration without an imaging function.

The foregoing embodiment is intended for an apparatus for tomography on an imaging object that is a cell cultured in a container, for example. This type of apparatus is also used for observation of living bodies such as observation of eye balls for medical purposes, for example. The present invention is also applicable to an imaging apparatus intended for such purposes.

The technical concept, in which a center wavelength in a conversion characteristic is set from a viewpoint of a balance between a resolution and an imaging possible range without determining a conversion characteristic uniquely from the spectrum characteristic of a light source, is also effective for an apparatus having one type of objective lens so not to switch the objective lens. Further, in imaging performed using the same objective lens, a spectrum conversion characteristic is switchable between a purpose placing importance on a resolution and a purpose placing importance on an imaging range, for example.

As seen from the specific embodiment illustrated and described above, according to the present invention, the center wavelength of a Gaussian distribution curve can be set at a longer wavelength than the center wavelength of a light source spectrum. In this configuration, a component of a long wavelength reaching a depth of an imaging object is used effectively in generation of an image, thereby allowing extension of an effective imaging possible range in the depth direction.

The center wavelength of a Gaussian distribution curve is settable in response to a resolution in a direction (horizontal direction) vertical to the optical axis of an objective lens that is determined by the center wavelength of a light source spectrum and the numerical aperture of the objective lens. While a resolution in the depth direction is changeable by setting the center wavelength of a Gaussian distribution curve, this resolution is not always used beneficially for an image unless it is balanced with a resolution in the horizontal direction. Making setting responsive to the resolution in the horizontal direction achieves image quality and an imaging range suitable for a purpose.

The signal processor can be configured to switch between several types of conversion characteristics having center wavelengths differing from each other in Gaussian distribution curves. This configuration allows a resolution and an imaging possible range in the depth direction to be switched in response to a purpose of use.

The optical coherence tomographic apparatus according to the present invention further includes a plurality of lenses having numerical apertures differing from each other, and a switcher that switches between the lenses and causes the switched lens to selectively function as an objective lens. The signal processor can be configured to switch a conversion characteristic in response to the selection of the lens. In this configuration, a resolution and an imaging possible range in the depth direction become adjustable in response to a resolution in the horizontal direction to be changed by switching between the objective lenses having different numerical apertures.

In a configuration applicable to this case, a Gaussian distribution curve depending on a conversion characteristic corresponding to one of the lenses having a maximum numerical aperture has a center wavelength closest to the center wavelength of the light source spectrum, and a Gaussian distribution curve depending on a conversion characteristic corresponding to one of the lenses having a smaller numerical aperture has a center wavelength at a longer wavelength. In this configuration, a maximum resolution in the depth direction is obtained by an objective lens having a large numerical aperture and providing a maximum resolution in the horizontal direction. Further, an objective lens providing a low resolution in the horizontal direction is configured to provide a resolution also low in the depth direction. By doing so, it becomes possible to extend an imaging possible range in the depth direction effectively.

The light source spectrum may have a component in a wavelength range from 700 to 1400 nanometers. Such a wavelength region exhibits high permeability to living bodies or cells and used effectively in ensuring wide imaging possible ranges for imaging living bodies or cells as imaging objects. Namely, the present invention is applied effectively if imaging objects are living bodies or cells in a culture solution.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

The present invention is applicable to all FD-OCT imaging techniques. In particular, the present invention is suitably applicable to the fields of medical science, biochemistry, and drug development in which imaging is performed for the purpose of observing/analyzing living bodies, cultured cells, and others.

REFERENCE SIGNS LIST 1 imaging apparatus (optical coherence tomographic apparatus)
20 imaging unit
21 light source
22 beam splitter (interference light generator)
23, 23a, 23b objective lens (lens)
24 reference mirror (interference light generator)
25 spectroscope (detector)
26 photo-detector (detector)
30 control unit (signal processor)
31 CPU
33 signal processor
43 lens switching mechanism (switcher)
220 optical fiber coupler (interference light generator)

The invention claimed is:

1. An optical coherence tomographic apparatus comprising:
a light source that emits light having a light source spectrum with a plurality of wavelength components;
a plurality of lenses having numerical apertures differing from each other;
a switcher that switches between the lenses and causes the switched lens to selectively function as an objective lens,
an interference light generator that includes a dividing/mixing optical device and a reference mirror, the dividing/mixing optical device (1) branching the light from the light source, (2) causing one branch light to enter an imaging object via the objective lens and another branch light to enter the reference mirror, (3) coupling reflected light reflected from the imaging object and collected by the objective lens to reflected light reflected from the reference mirror, and (4) generating interference light;
a detector that detects the interference light; and
a processor that determines a reflected light intensity distribution of the imaging object on the basis of the spectrum of the detected interference light, wherein
the processor performs spectrum conversion, the spectrum conversion having a conversion characteristic with which the light source spectrum is converted to a Gaussian distribution curve, on the spectrum of the interference light, and determines the reflected light intensity distribution by Fourier-transforming a spectrum resulting from the spectrum conversion,
in the conversion characteristic, the light source spectrum and the Gaussian distribution curve have center wavelengths differing from each other, and
the processor is configured to select the conversion characteristic with which the light source spectrum is converted to the Gaussian distribution curve from several types of conversion characteristics having center wavelengths differing from each other in Gaussian distribution curves based on the switched lens.

2. The optical coherence tomographic apparatus according to claim 1, wherein the center wavelength of the Gaussian distribution curve is set at a longer wavelength than the center wavelength of the light source spectrum.

3. The optical coherence tomographic apparatus according to claim 1, wherein
the processor performs the spectrum conversion using the Gaussian distribution curve having the center wavelength corresponding to a resolution in a direction vertical to an optical axis of the objective lens, the resolution depending on the center wavelength of a light source spectrum and the numerical aperture of the objective lens.

4. The optical coherence tomographic apparatus according to claim 1, wherein
a Gaussian distribution curve depending on a conversion characteristic corresponding to one of the lenses having a maximum numerical aperture has a center wavelength closest to the center wavelength of the light source spectrum, and
a Gaussian distribution curve depending on a conversion characteristic corresponding to one of the lenses having a smaller numerical aperture has a center wavelength at a longer wavelength.

5. The optical coherence tomographic apparatus according claim 1, wherein
the light source spectrum has a component in a wavelength range from 700 to 1400 nanometers.

6. An optical coherence tomographic method, comprising:
switching between lenses and causes the switched lens to selectively function as an objective lens, the lenses having numerical apertures differing from each other;
branching light having a light source spectrum with a plurality of wavelength components, causing one branch light to enter an imaging object via the objective lens, collecting light reflected from the imaging object with the objective lens, and coupling the collected light to different branch light, thereby generating interference light; and
detecting the interference light and determining a reflected light intensity distribution of the imaging object on the basis of the spectrum of the detected interference light, wherein spectrum conversion, having a conversion characteristic with which the light source spectrum is converted to a Gaussian distribution curve, is performed on the spectrum of the interference light, a spectrum resulting from the spectrum conversion is Fourier-transformed to determine the reflected light intensity distribution, in the conversion characteristic, the light source spectrum and the Gaussian distribution curve have center wavelengths differing from each other, and the conversion characteristic with which the light source spectrum is converted to the Gaussian distribution curve is selected from several types of conversion characteristics having center wavelengths differing from each other in Gaussian distribution curves based on the switched lens.

7. The optical coherence tomographic method according to claim 6, wherein the imaging objects are living bodies or cells in a culture solution.

\* \* \* \* \*